United States Patent
Flamand et al.

(10) Patent No.: US 7,282,341 B2
(45) Date of Patent: Oct. 16, 2007

(54) ASSAY FOR THE DIAGNOSIS OF FLAVIVIRAL INFECTION USING ANTIBODIES WITH HIGH AFFINITY FOR NS1 PROTEIN OF FLAVIVIRUS IN HEXAMERIC FORM

(75) Inventors: Marie Flamand, Paris (FR); Françoise Megret, Paris (FR); Sophie Alcon, Livry-Gargan (FR); Antoine Talarmin, Paris (FR); Philippe Despres, Garenne-Colombes (FR); Vincent Deubel, Vanves (FR)

(73) Assignee: Institut Pasteur, Paris (FR)

( * ) Notice: Subject to any disclaimer, the term of this patent is extended or adjusted under 35 U.S.C. 154(b) by 346 days.

(21) Appl. No.: 11/017,048

(22) Filed: Dec. 21, 2004

(65) Prior Publication Data

US 2005/0186562 A1 Aug. 25, 2005

Related U.S. Application Data

(62) Division of application No. 09/980,839, filed as application No. PCT/FR00/01620 on Jun. 9, 2000, now Pat. No. 6,870,032.

(30) Foreign Application Priority Data

Jun. 9, 1999 (FR) ................................. 99 07290
Jun. 10, 1999 (FR) ................................. 99 07361

(51) Int. Cl.
*C12Q 1/70* (2006.01)
*A61K 39/12* (2006.01)
*A61K 39/42* (2006.01)

(52) U.S. Cl. .................... 435/7.1; 435/5; 424/218.1; 424/147.1

(58) Field of Classification Search ................ None
See application file for complete search history.

(56) References Cited

U.S. PATENT DOCUMENTS 4,281,061 A  7/1981 Zuk et al. .................... 435/7

FOREIGN PATENT DOCUMENTS

EP  0 402 116 A1  12/1990

WO  WO93/22440  11/1993

OTHER PUBLICATIONS

Flamand et al. Journal fo Virology, Jul. 1999, 73(7):6104-6110.*
Young et al. Journal of Clinical Microbiology, Mar. 2000, 38(3):1053-1057.*
Schlesinger et al. The Journal of Immunology, Oct. 1985, 135(4):2805-2809.*
Crooks, Alan J. et al., , "The NS1 Protein of Tick-Borne Encephalitis Virus Forms Multimeric Species Upon Secretion From The Host Cell" Journal of General Virology (1994), 75. pp. 3453-3460.
Falconar, A.K.I., et al., "Precise Location of Sequential Dengue Virus Subcomplex And Complex B Cell Epitopes On The Nonstructural-1 Glycoprotein", Arch Virol (1994) 137: pp. 315-326.
Falconar, A.K.I., et al., "Production of Dimer-Specific and Dengue Virus Group Cross-Reactive Mouse Monoclonal Antibodies to the Dengue 2 Virus Non-Structural Glycoprotein NS1", Short Communication, (1991) pp. 962-965.
Falconar, A.K.I., "Immunoaffinity Purification of Native Dimer Forms of the Flavivirus Non-Structural Glycoprotein, NS1", Journal of Virological Methods, 30 (1990) pp. 323-332.
Jacobs, S.C., et al., "High-Level Expression of the Tick-Borne Encephalitis Virus NS1 Protein by Using an Adenovirus-Based Vector: Protection Elicited in a Murine Model", Journal of Virology, Apr. 1992 pp. 2086-2095.
Flamand, M. et al., "Purification and Renaturation of Japanese Encephalitis Virus Nonstructural Glycoprotein NS1 Overproduced by Insect Cells", Protein Expression and Purification 6, (1995) pp. 519-527.
Hall, R.A. et al., "Immunoaffinity Purification of the NS1 Protein of Murray Valley Encephalitis Virus: Selection of the Appropriate Ligand and Optimal Conditions for Elution", Journal of Virological Methods, 32 (1991) pp. 11-20.

* cited by examiner

*Primary Examiner*—Stacy B. Chen
(74) *Attorney, Agent, or Firm*—Finnegan, Henderson, Farabow, Garrett & Dunner LLP

(57) ABSTRACT

The invention concerns a method for early detection of a flavivirus-induced infection, comprising the detection of the flavivirus non-structural glycoprotein NS1 in a biological sample during the clinical phase of the infection, by an immunological method using at least two identical or different antibodies, the first antibody consisting of polyclonal or monoclonal antibodies pre-selected for their high affinity for said NS1 protein hexameric in shape.

6 Claims, 9 Drawing Sheets

FIG. 2

SEQ ID N°1 : NS1 PROTEIN OF DENGUE VIRUS SEROTYPE 1

Figure 1A:
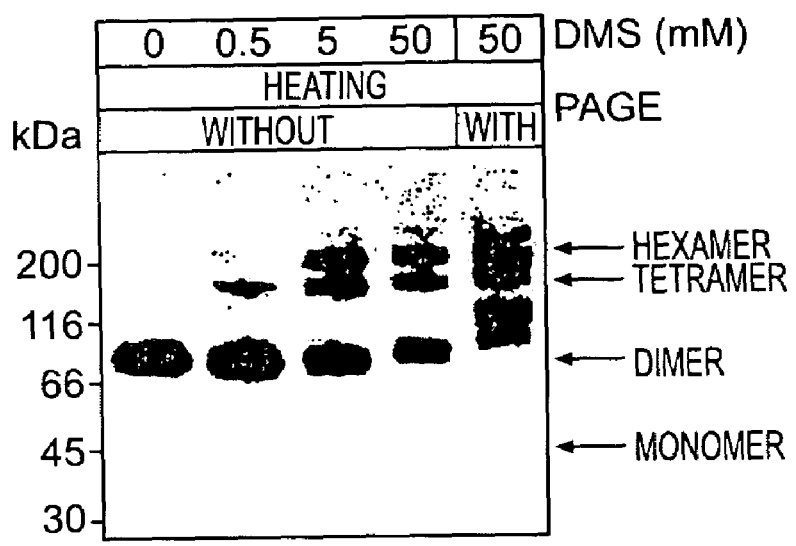

```
1/1                                    31/11
atg agg gcg tcg ctt atg acg tgc att gca gtt ggc atg aca ctg tac cta
Met arg ala ser leu met thr cys ile ala val gly met thr leu tyr leu
61/21                                  91/31
gga gtc acg gtt caa gcg gac tcg gga tgt gta atc aac tgg aag gaa ctc aaa
gly val met val gln ala asp ser gly cys val ile asn trp lys glu leu lys
121/41                                 151/51
tgt gga agt ggc att ttt gtc act aat gaa gtc cac tgg aca gag caa tac aaa ttc
cys gly ser gly ile phe val thr asn glu val his trp thr glu gln tyr lys phe
181/61                                 211/71
cag gct gac tcc cca aaa aga ctg tca gca gcc att ggg gag tgg gag ggc gtg
gln ala asp ser pro lys arg leu ser ala ala ile gly glu trp glu gly val
241/81                                 271/91
tgt gga att cga tca gcc acg cgt ctt gag aac att atg aag caa ata tca aat gaa
cys gly ile arg ser ala thr arg leu glu asn ile met lys gln ile ser asn glu
301/101                                331/111
ccg aac cac att cta gaa aat gac atg aaa ttc aca gtc gta gga gat gct aat
leu asn his ile leu glu asn asp met lys phe thr val val gly asp ala asn
361/121                                391/131
gga att tcg gcc cag ggg aaa aaa atg atc agg cca taa ccc atg gaa cac aaa tac tca
gly ile leu ala gln gly lys lys met ile arg pro gln pro met glu his lys tyr ser
421/141                                451/151
tgg aaa agc tgg gga aag gcc aag atc ata gga gca gac aca cag gac acc ttc atc
trp lys ser trp gly lys ala lys ile ile gly ala asp thr gln asp thr phe ile
481/161                                511/171
atc gac ggc cca gac act cca gaa tgc ccc gat gac cag aga gcg tgg aac att tgg gaa
ile asp gly pro asp thr pro glu cys pro asp asp gln arg ala trp asn ile trp glu
541/181                                571/191
gtt gag gac tat ggg ttt gga att ttc acg aca aac ata ttc ctg aaa ttg cgt gac tcc
val glu asp tyr gly phe gly ile phe thr thr asn ile phe leu lys leu arg asp ser
```

FIG. 2 CONTINUED

```
601/201
tac acc caa atg tgt gac cac cgg cta atg
tyr thr gln met cys asp his arg leu met
661/221
cat gct gac acg ggg tac tgg ata gaa agt
his ala asp met gly tyr trp ile glu ser
721/241
gcc tcc ttc aca gaa gtc aag aca tgc att
ala ser phe ile glu val lys thr cys ile
781/261
gga gtt ttg gaa agt gaa atg ata atc cca
gly val leu glu ser glu met ile ile pro
841/281
aat tac aga cca ggg tat ttc aca caa aca
asn tyr arg pro gly tyr phe thr gln thr
901/301
ttg gat ttt gac tcg tgt gaa ggc acc aca
leu asp phe asp ser cys glu gly thr thr
961/321
ggt cca tct ctc aga act aca aca aca aca
gly pro ser leu arg thr thr thr thr thr
1021/341
tcc tgc acg tta ccc ccc tta cgc ttc aga
ser cys thr leu pro pro leu arg phe arg
1081/361
atc aga cca gtt aag gag aag gag gag aac
ile arg pro val lys glu lys glu glu asn 631/211
tca gct gcc gtc aag gac agc aag gca gtc
ser ala ala val lys asp ser lys ala val
691/231
gaa aag aac gag aag tgg acc tgg cta gcg aga
glu lys asn glu lys trp thr trp leu ala arg
751/251
tgg ccg aaa tcc cac act cta tgg agt aat
trp pro lys ser his thr leu trp ser asn
811/271
aag ata tat gga gga cca aca cct cag cac
lys ile tyr gly gly pro thr pro gln his
871/291
gca ggg gca gtt gtt aca cac tgg cac cta ggt aag ttg gaa
ala gly ala val val thr his trp his leu gly lys leu glu
931/311
gtt gtt aca aca gtc gat gaa cat tgt gga aat cga
val val thr thr val asp glu his cys gly asn arg
991/331
gga aag aca acg aag ata atc cat gaa tgg tgt tgc aga
gly lys thr thr lys ile ile his glu trp cys cys arg
1051/351
gga gaa gac gly glu asp ggg ttc tgg tat ggc atg gaa
gly glu asp gly glu asp gly cys trp tyr gly met glu
1111/371
cta gtt agg tca atg gtc tct gca taa
leu val arg ser met val ser ala
```

| I.D. | IHA | | | | MAC ELISA | O.D. DURING NS1 ASSAY | | |
|---|---|---|---|---|---|---|---|---|
| | D1 | D2 | D3 | D4 | | 10th | 30th | 90th |
| NOL 1 | 0 | 0 | 0 | NR | NEG | 0.24 | 0.16 | 0.13 |
| NOL 2 | 10 | 40 | 10 | NR | POS | 0.13 | 0.10 | 0.09 |
| NOT 1 | 0 | 0 | 0 | NR | NEG | 0.53 | 0.26 | 0.14 |
| NOT 2 | 40 | 160 | 160 | NR | POS | 0.01 | 0.01 | 0.01 |
| MONT 1 | 0 | 0 | 0 | NR | NEG | 1.02 | 0.67 | 0.44 |
| MONT 2 | 320 | 40 | 20 | NR | POS | 0.03 | 0.02 | 0.02 |
| BAIL 1 | 0 | 0 | 0 | NR | NEG | 1.20 | 0.83 | 0.64 |
| BAIL 2 | 80 | 160 | 160 | NR | POS | 0.06 | 0.07 | 0.08 |
| LEG 1 | 0 | 0 | 0 | 0 | NEG | 1.50 | 1.09 | 0.56 |
| LEG 2 | 160 | 80 | 160 | NR | POS | 0.05 | 0.05 | 0.06 |
| SGH 1 | 0 | 0 | 0 | NR | NEG | 0.76 | 0.54 | 0.26 |
| SGH 2 | 80 | 640 | 160 | NR | POS | 0.03 | 0.02 | 0.03 |
| DETT 1 | 0 | 0 | 0 | NR | NEG | 0.23 | 0.13 | 0.09 |
| DETT 2 | 640 | 160 | 160 | NR | POS | 0.05 | 0.05 | 0.04 |
| CON 1 | 0 | 0 | 0 | 0 | NEG | 0.23 | 0.10 | 0.10 |
| CON 2 | 1280 | 1280 | 1280 | 1280 | POS | 0.12 | 0.07 | 0.03 |
| BOLL 1 | 0 | 0 | 0 | 0 | NEG | 0.42 | 0.48 | 0.23 |
| BOLL 2 | 1280 | 1280 | 1280 | 1280 | POS | 0.09 | 0.08 | 0.20 |
| PORN 1 | 0 | 0 | 0 | NR | NEG | 0.54 | 0.54 | 0.44 |
| PORN 2 | 1280 | 1280 | 1280 | 1280 | POS | 0.02 | 0.02 | 0.01 |
| PAJ 1 | 0 | 0 | 0 | 0 | NEG | 1.71 | 1.27 | 0.73 |
| PAJ 2 | 1280 | 1280 | 1280 | 1280 | POS | 0.07 | 0.07 | 0.06 |
| PLAQ 1 | 10 | 20 | 20 | NR | NEG | 1.32 | 0.86 | 0.43 |
| PLAQ 2 | 1280 | 1280 | 1280 | 1280 | POS | 0.28 | 0.18 | 0.18 |
| GOH 1 | 10 | 40 | 20 | NR | NEG | 1.35 | 1.15 | 0.26 |
| GOH 2 | 1280 | 1280 | 1280 | 1280 | POS | 0.06 | 0.09 | 0.14 |
| BEAU 1 | 10 | 20 | 20 | 40 | POS | 1.01 | 0.76 | 0.53 |
| BEAU 2 | 1280 | 1280 | 1280 | 1280 | POS | 0.07 | 0.08 | 0.07 |

*FIG. 3*

| | ELISA NS1+ | | ELISA NS1- | | % POSITIVITY FOR NS1 |
|---|---|---|---|---|---|
| | MAC IgM- | MAC IgM+ | MAC IgM- | MAC IgM+ | |
| $D_0$ | 2 | | | | - |
| $D_1$ | 13 | | 3 | | 81.2 |
| $D_2$ | 8 | 1 | 6 | | 64.3 |
| $D_3$ | 10 | 4 | 1 | | 93 |
| $D_4$ | 4 | 6 | | | 100 |
| $D_5$ | 1 | 6 | | | 100 |
| $D_6$ | | 4 | | 1 | 80 |
| $D_7$ | | 1 | | 1 | - |
| $D_8$ | | | | 1 | - |
| $D_9$ | | 1 | | 2 | - |
| $D_{11}$ TO $D_{66}$ | | | | 33 | 0 |

FIG. 4

|  | F22 | G18 |
|---|---|---|
| REACTIVITY IN ELISA (DEN1 NSI) | | |
| PURIFIED SOLUBLE HEXAMERIC NS1 | + | + |
| IMMUNOCAPTURED SOLUBLE HEXAMERIC NS1 | + | + |
| REACTIVITY IN INDIRECT IMMUNOFLUORESCENCE | | |
| DEN1 - INFECTED CELLS | + | + |
| DEN2 - INFECTED CELLS | - | - |
| DEN3 - INFECTED CELLS | - | + |
| DEN4 - INFECTED CELLS | - | - |
| ISOTYPE | IgG1 K | IgG1 K |
| AFFINITY CONSTANT | $2.7.10^{-9}$M | $3.10^{-11}$M |
| EPITOPE | A | B |

*FIG. 6*

| PATIENT NO. | D | IgM | O.D. WITH MONOCLONALS | | | O.D. WITH POLYCLONALS | | |
|---|---|---|---|---|---|---|---|---|
| | | | 10th | 30th | 90th | 10th | 30th | 90th |
| 314 | 1 | - | 0.33 | 0.22 | 0.10 | 0.11 | 0.07 | 0 |
| 231 | 3 | - | 0.80 | 0.68 | 0.33 | 0.41 | 0.22 | 0.05 |
| 292 | 3 | - | 0.84 | 0.74 | 0.43 | 0.47 | 0.33 | 0.16 |
| 304 | 3 | + | 1.23 | 0.92 | 0.59 | 0.66 | 0.41 | 0.22 |
| 371 | 3 | + | 1.10 | 1.10 | 0.81 | 0.68 | 0.49 | 0 |
| 88 | 4 | - | 1.24 | 1.27 | 1.19 | 1.13 | 0.95 | 0.35 |
| 106 | 5 | + | 1.28 | 1.25 | 1.26 | 0.95 | 0.86 | 0.16 |
| 383 | 13 | + | 0.04 | 0.04 | 0.04 | 0.09 | 0.07 | 0.01 |
| 222 | 29 | + | 0.01 | 0.01 | 0.02 | 0.07 | 0.06 | 0 |
| 267 | 50 | + | 0.01 | 0.01 | 0 | 0.06 | 0.05 | 0.03 |

*FIG. 7*

| SERUM NO. | OD MAC IgM FJ | OD NS1 FJ | VIRAL ISOLATION |
|---|---|---|---|
| 1 | 0.306 | 1.13 | + |
| 2 | 0.535 | 1.20 | + |
| 3 | 0.364 | 0.6 | |
| 4 | 0.578 | 0.65 | |
| 5 | 0.741 | 0.75 | |
| 6 | 0.968 | | |
| 7 | 1.013 | | |
| 8 | 1.101 | | |
| 9 | 1.159 | | |
| 10 | 1.278 | 0.61 | |
| 111 | 1.336 | | |
| 12 | 1.448 | | |
| 13 | 1.466 | | |
| 14 | 1.501 | | |
| 15 | 1.523 | 1.19 | |
| 16 | 1.587 | | |
| 17 | 1.940 | | |
| 18 | 2.109 | | |

*FIG. 8*

ASSAY FOR THE DIAGNOSIS OF FLAVIVIRAL INFECTION USING ANTIBODIES WITH HIGH AFFINITY FOR NS1 PROTEIN OF FLAVIVIRUS IN HEXAMERIC FORM

This is a divisional of application Ser. No. 09/980,839, filed Dec. 7, 2001, now U.S. Pat. No. 6,870,032, and PCT International Application No. PCT/FR00/01620, filed Jun. 9, 2000, which claims priority of French Applicant No. FR 99 07361, filed Jun. 10, 1999, and French Application No. FR 99 07290, filed Jun. 9, 1999, all of which are incorporated herein by reference.

The present invention relates to a method for the early detection of flaviviruses, in particular of the dengue virus, and to the application thereof.

Dengue is an acute febrile tropical disease and the virus which causes it is an arbovirus which is transmitted by mosquitoes. The vectors of the disease are mosquitoes of the *Aedes* genus, in particular *Aedes aegypti*, which most commonly leave their larvae in domestic and peridomestic areas. The responsible virus, isolated in 1951, has been classified into four different antigenic types (DEN1, DEN2, DEN3 and DEN4) It belongs to the Flaviviridae family, genus flavivirus.

More than two billion inhabitants live in endemic regions and the number of individuals infected by the virus is thought to be more than 100 million per year. Dengue is in particular responsible for 500 000 hospitalizations and for several tens of thousands of deaths annually, mostly children.

After an incubation of five to eight days, the clinical signs generally begin suddenly and consist of the appearance of undifferentiated fever (DF dengue fever) accompanied by severe headaches, lumbago, muscle and joint pain and also shivering. From the third to the fifth day of the febrile phase, a congestive maculopapular rash may appear for three to four days (conventional dengue).

In its severe form, the infection may result in the appearance of a hemorrhagic syndrome (DHF or dengue hemorrhagic fever), characterized by increased vascular permeability and deregulation of hemostasis. Although, in the majority of cases, the disease generally evolves favorably within a week, it may turn out to be fatal in the event of hypovolemic shock (DSS or dengue shock syndrome). These complications may be due to the presence of preexisting immunity, acquired in particular during a primary infection with a heterologous dengue virus (different serotype). Specifically, two different types of serological response are identified in individuals infected with dengue: individuals who have never suffered a flavivirus infection and have not been vaccinated against another flavivirus (yellow fever virus, Japanese encephalitis virus for example) will exhibit a primary response, characterized by a slow appearance of antibodies specific for the virus responsible for the infection; individuals who have already suffered a flavivirus infection (other dengue serotype for example) or have been vaccinated against another flavivirus will exhibit a secondary response, characterized by the rapid appearance of antibodies.

The infectious agent is the dengue virus which belongs to the Flaviviridae family, to which the yellow fever virus and the Japanese encephalitis virus also belong (T. P. Monath et al., (1996) Flaviviruses in B. N. Fields, D. M. Knipe, P. M. Howly et al. (eds.) "Fields Virology" Philadelphia: Lippincott Raven Press Publishers). These viruses have a single-strand RNA with positive polarity which comprises 11 000 nucleotides and which encodes a polyprotein of approximately 3400 amino acids. It is separated into three structural proteins and seven nonstructural proteins NS1, NS2A, NS2B, NS3, NS4A, NS4B and NS5, during co-translational and post-translational cleavage by viral and cellular proteases. The NS1 nonstructural protein was identified for the first time in 1970 by P. K. Russel et al. (*J. Immunol.*, (1970), 105, 838-845) and characterized in 1985 by G. W. Smith et al. (*J. Gen Virol.*, (1985), 66, 559-571). This glycoprotein, which is highly conserved in the flavivirus genus (T. P. Monath already mentioned), in particular in the four dengue virus serotypes, exists in an intracellular form and in an extracellular form. The intracellular form is thought to be involved in the early phases of replication of the virus (Hall R. A. et al., *J. Virol.* (1999), 73, 10272-10280; Rice C. M. et al., *J. Virol.* (1997), 71, 291-298; Rice C. M. et al., *J. Virol.*, (1996), 222, 159-168; Rice C. M. et al., *J. Virol.*, (1997), 71, 9608-9617). Before being transported to the plasma membrane, the NS1 protein undergoes dimerization. In mammalian cells, but not in insect cells, a portion Of the NS1 protein is released into the extracellular medium, either primarily in the form of a soluble protein, or secondarily in a microparticulate form. When it is in a soluble form, the protein exists in the form of an oligomer, in particular of a pentamer or of a hexamer (Crooks A. J. et al. *J. Chrom.* (1990), 502, 59-68 and *J. Gen. Virol.* (1994), 75, 3453-3460). At the current time, the biological function of the NS1 protein is unknown.

Several studies suggest that the NS1 protein is immunodominant in nature in the protective immune response against flavivirus infections. Experiments carried out with a certain number of flaviviruses, such as the yellow fever, dengue, Japanese encephalitis and tick-borne encephalitis viruses, have shown partial or total protection against a lethal dose of homologous virus in animals vaccinated using the subunit NS1 protein or the NS1 protein produced by virus vectors, of the vaccinia or adenovirus type (Schlesinger et al., J. Virol (1986), 60, 1153-1155; *J. Gen. Virol.*, (1987), 68, 853-857; Falgout et al. *J. Virol.*, (1990), 64, 4356-4363; Jacobs et al. *J. Virol.*, (1992), 66, 2086-2095; Hall et al. *J. Gen. Virol.*, (1996), 77, 1287-1294; Konishi et al., *Virology*, (1991), 185, 401-410).

Passive immunization of mice with monoclonal anti-NS1 antibodies has also made it possible to obtain a certain degree of protection (Schlesinger et al., *J. Immunol.* (1985), 135, 2805-2809; Gould et al. *J. Gen. Virol.*, (1986), 67, 591-595; Henchal et al., *J. Gen. Virol.*, (1988), 69, 2101-2107). The role of anti-NS1 antibodies in the protection is not entirely known. It may be that the NS1 proteins at the surface of infected cells are recognized by complement-fixing antibodies, leading to lysis of the infected cells (Schlesinger et al., *Virology*, (1993), 192, 132-141).

No specific treatment exists and the care given to the patient is uniquely symptomatic. In the case of conventional dengue, the treatment is based on the administration of analgesics and antipyretics. In the case of DHF, the treatment consists of an infusion to compensate for the plasma leakage, combined with correction of hydroelectric problems and reinitiation of diuresis.

There is no commercially available vaccine against the dengue virus. On the other hand, protection assays with attenuated strains of the 4 dengue virus serotypes have been carried out by N. Bhamarapravati et al. (Dengue and Dengue haemorrhagic fever (1997), 367-377), with unsatisfactory results. Prevention is therefore based solely on combating the vector. This combat combines larval destruction and "adulticide" spraying.

In the absence of a vaccine, it is necessary to monitor epidemics and to prevent the abovementioned complications; to do this, active monitoring programs have in particular been set up by the World Health Organization, and essentially comprise the monitoring of cases of fever and of vector insects, and the serological and virological screening of individuals having a fever and suspected of being infected with the dengue virus.

The etiology of dengue is sometimes tricky to affirm when a patient exhibits a dengue-like undifferentiated febrile syndrome, the cause of which may be another arbovirus, viruses which cause eruptive fevers such as the flu, or nonviral pathogens which are agents of diseases such as leptospirosis and even malaria. Only a laboratory test can provide the diagnosis.

At the current time, several tests exist for diagnosing dengue. However, in order to obtain an interpretable result, it is necessary to combine several methods:

isolation of the virus, by conventional virology techniques, in particular by infection of cell cultures or propagation in the brain of young mice or amplification by inoculation into mosquitoes, and examination, for example, by immunofluorescence. These methods have the drawback of being difficult to carry out and of depending on the sample being taken early and on good conditions of conservation; in addition, the first results cannot be obtained in less than a week; in order to overcome these drawbacks, use may be made of an RT/PCR test (V. Deubel, *L'eurobiologiste* (1997), volume XXXI, 37-155); however, this means is not always reliable and cannot be used routinely in the countries to which the dengue virus relates, for reasons of cost and equipment;

serological tests; the earliest serological diagnosis consists in searching for IgMs specific for viral antigens using the MAC-ELISA (*immunoglobulin M Antibody Capture Enzyme-Linked ImmunoSorbent Assay*) technique. Detection of these IgMs several days after the beginning of the symptoms makes it possible to establish a diagnosis of probability of infection with a flavivirus. Antibodies of the IgG type appear later than antibodies of the IgM type. In all cases, the search for antibodies requires two samples: one at the beginning of the clinical signs, the other 10 to 28 days later, so as to demonstrate serological conversion via an inhibition of hemagglutination reaction (IHA) or by ELISA.

Simple and inexpensive immunological tests have also been proposed, which can be used in the countries at risk and which use, as a specific immunological reagent, peptides derived from the NS1 nonstructural protein characteristic of flaviviruses. Thus, U.S. Pat. No. 5,824,506 describes a method using peptides derived from the NS1 nonstructural protein, which makes it possible to detect the antibodies induced by the presence of the dengue virus; however, the peptides selected essentially recognize samples obtained from convalescent individuals and also recognize patients infected for the second time better than those infected for the first time; these disappointing results may be explained by the fact that the peptides used are not representative of the antigenic characteristics of the native protein and therefore lead to poor recognition of the antibodies being sought.

In all cases, only late confirmation of an infection with a flavivirus may be given.

A report from the *Sir Albert Sakzewski Virus Research Center, Royal Children's Hospital*, (A. Falconar, 1991) describes the search for the NS1 nonstructural glycoprotein in the serum of patients infected with the DEN2.virus. The authors of this report have developed a double-sandwich ELISA assay in which a rabbit serum containing polyclonal anti-NS1 antibodies, used as capture antibodies, is immobilized on a microtitration plate. The antigen captured is detected using mouse monoclonal antibodies directed against the NS1 protein, either of the dengue virus of the DEN2 type, or specific for the serological complex of dengue; the formation of the antigen/antibody complex is revealed using peroxidase-conjugated goat anti-mouse IgG. With this method, the authors have shown, by using the degraded or purified dimeric NS1 protein as the standard, that the sensitivity of detection of the assay is approximately 4 ng/ml with the DEN2 monoclonal antibodies as the revelation probe and approximately 60 ng/ml with the group monoclonal antibodies.

However, this assay does not make it possible to detect the NS1 protein either in the case of primary infections in the acute or convalescent phase, or in secondary infections in the convalescent phase in which there is a high titer of anti-NS1 antibodies; the authors have concluded therefrom that the NS1 protein must be present in large amounts only in cases of secondary infections, this being transiently, during the infection.

Now, the inventors have developed a method for purifying the NS1 protein of a flavivirus, in the hexameric form, which has allowed them to select antibodies specific for this protein in hexameric form, and to show, surprisingly, that these antibodies are tools of choice for demonstrating the various problems of the circulating NS1 protein in the context of an infection with a flavivirus, in particular in the early phases in which the specific antibody response is undetectable, especially during primary infections with the dengue virus.

Consequently, the inventors have given themselves the aim of providing a method for the early detection of a flaviviral infection, which corresponds to practical needs better than the methods of the prior state of the art, i.e. a method which is reliable, rapid and inexpensive and which makes it possible to adapt the medical care in time.

Consequently, a subject of the present invention is a method for the early detection of a flaviviral infection, characterized in that it comprises detecting the NS1 non-structural glycoprotein of a flavivirus in a biological sample, throughout the duration of the clinical phase of the infection, by an immunological method using at least two antibodies, which may be identical or different, the first antibody or antibody for capturing the NS1 glycoprotein consisting of antibodies chosen from the group consisting of:

polyclonal antibodies preselected by immunocapture on the NS1 protein of said flavivirus, in the hexameric form, and mixtures of anti-NS1 monoclonal antibodies preselected for their high affinity for the NS1 protein of said flavivirus, in the hexameric form, said monoclonal antibodies then being purified, the second antibody or revelation antibody being chosen from the group consisting of:

polyclonal antibodies directed against the NS1 protein in the hexameric form, and a mixture of monoclonal antibodies directed against the NS1 protein in the hexameric form.

For the purpose of the present invention, the expression "hexameric form of the NS1 protein of a flavivirus" is intended to mean the native protein obtained from the culture supernatant of mammalian cells infected with said flavivirus or transformed using an expression system comprising the gene of the NS1 protein of said flavivirus, and purified according to the method of the invention as described-below. This hexameric form of said NS1 protein, which differs from other forms such as the monomeric form or the dimeric form of said protein, is demonstrated using electrophoresis or chromatography techniques such as those described in FIG. 1.

For the purpose of the present invention, the expression "polyclonal and monoclonal antibodies directed against the NS1 protein of a flavivirus" is intended to mean antibodies obtained by immunizing a nonhuman mammal,
either with an NS1 protein in the hexameric form,
or with a live or inactivated flavivirus, said polyclonal antibodies being selected for their affinity for the NS1 protein in the hexameric form and purified in a single step, and said monoclonal antibodies being preselected for their high affinity for the NS1 protein in the hexameric form and then purified by conventional techniques, in particular by ion exchange or affinity chromatography.

For the purpose of the present invention, the expression "affinity of a monoclonal antibody for the NS1 protein in the hexameric form" is intended to mean the concentration of said protein required to saturate 50% of the sites of the antibody; this is measured by the affinity constant of said antibody, according to the protocol described in example 5.

For the purpose of the present invention, the term "high affinity" is intended to mean an affinity for which the constant is less than $10^{-8}$ M.

Surprisingly, the use, for detecting the NS1 protein in a biological sample, of polyclonal antibodies selected and purified by immunocapture on the NS1 protein in the hexameric form, or of monoclonal antibodies which have a high affinity for the NS1 protein in the hexameric form and which are purified, instead of a total hyperimmunized rabbit serum, makes it possible to significantly improve the sensitivity of the method and to detect the NS1 protein circulating in the blood of patients, from the early stage of infection, both during a primary infection and a secondary infection.

The method according to the present invention has a certain number of advantages:
- it may be carried out early: the presence of the NS1 glycoprotein is revealed during the clinical phase, before the antibody response is detectable,
- it is sensitive:, it is possible to detect as little as less than 1 ng of protein/ml of serum, which makes it possible to detect the circulating NS1 protein in the early phase of primary infections,
- it is rapid: an answer can be obtained within a day,
- it is relatively inexpensive and can therefore be used in the countries at risk,
- it makes it possible to distinguish vaccinated individuals from individuals recently infected with a flavivirus, since the NS1 protein will be absent in vaccinated individuals in which the antibodies may still be detectable.

According to an advantageous embodiment of said method, the flaviviral infection is an infection with the dengue virus.

According to another advantageous embodiment of said method, the first antibody is preferably attached to a suitable solid support and the second antibody is optionally conjugated to a suitable label.

According to another advantageous embodiment of said method, when the second antibody is not conjugated to a label, its binding to the NS1 protein attached to the solid support is then detected with a third antibody, conjugated to a suitable label, said third antibody being a conventionally used antibody, such as for example an IgG directed against the second antibody and produced in particular in the goat, the pig or the donkey.

Among the labels used, mention may be made, by way of example, of fluorescent labels, the biotin/streptavidin system, nonisotopic labels or enzymes, such as for example horseradish peroxidase or alkaline phosphatase.

According to another advantageous embodiment of said method, said third antibody is conjugated to an enzyme.

According to another advantageous embodiment of said method,
the first antibody, or capture antibody, consists of mouse polyclonal antibodies selected by immunocapture on the NS1 protein of the dengue virus, said protein being in the hexameric form, and
the second antibody, or antibody for detecting the presence of NS1 in the biological sample to be analyzed, consists of polyclonal antibodies from a rabbit immunized with the NS1 protein of the dengue virus, said protein being in the hexameric form, the attachment of said second antibody being revealed with a third antibody, consisting of antibodies conjugated to peroxidase and directed against the second antibody.

According to another even more advantageous embodiment of said method, the mouse polyclonal antibodies are purified by immunocapture on the hexameric NS1 protein of dengue serotype 1.

A subject of the present invention is also a kit or boxed set for diagnosing a flaviviral infection, characterized in that it comprises:
at least one capture antibody and at least one revelation antibody as defined above,
at least one positive control consisting of the NS1 protein of a flavivirus and/or of various serotypes depending on the flavivirus, said protein being in a hexameric form, and
at least one negative control consisting of a normal human serum.

According to an advantageous embodiment of the boxed set for diagnosis according to the invention, said NS1 protein in the hexameric form is obtained from a culture supernatant either from infected mammalian cells or from mammalian cells transfected with a recombined plasmid comprising the gene of the NS1 protein or a fragment of said gene or a fragment of the flaviviral genome, said fragments being capable of expressing all or part of the NS1 protein.

According to another advantageous embodiment of the boxed set for diagnosis according to the invention, the NS1 protein is that of the dengue virus.

According to an even more advantageous embodiment of said boxed set for diagnosis, the plasmid is the pcIneo-NS1.FGA plasmid which was deposited with the Collection Nationale de Cultures et de Microorganismes [National collection of cultures and microorganisms] held by the Institut Pasteur under the number I-2220, dated Jun. 7, 1999.

A subject of the present invention is also a method for purifying the NS1 protein of a flavivirus, in the hexameric form, from a culture supernatant either of infected mammalian cells or of mammalian cells transfected with a recombined plasmid comprising the gene of the NS1 protein of a flavivirus or a fragment of said gene or a fragment of the flaviviral genome, said fragments being capable of expressing the NS1 protein in a hexameric form, characterized in that, prior to the purification of the NS1 protein using conventional techniques such as affinity chromatography, the soluble form of the NS1 protein is separated from the microparticulate form of said protein, by treatment with a precipitating agent and then by centrifugation.

For example, the centrifugation is carried out at a speed greater than or equal to 10 000 g.

For the purpose of the present invention, the term "precipitating agent" is intended to mean an agent which precipitates specifically microparticulate proteins or cellular debris, such as for example polyethylene glycol, said agent being used under conventional conditions which make it possible to separate soluble proteins and microparticulate proteins or cellular debris.

In a preferred embodiment of said purification method, the hexameric NS1 protein is that of the dengue virus, in particular dengue virus serotype 1.

A subject of the present invention is also an immunogenic composition, characterized in that it comprises, as the active principle, the NS1 protein of a flavivirus, in the hexameric form, optionally associated with other proteins, in combination with at least one pharmaceutically acceptable vehicle.

In a preferred embodiment of the immunogenic composition according to the present invention, the immunogenic composition comprises at least one mixture of the-NS1 proteins in the hexameric form corresponding to the various dengue virus serotypes.

A subject of the present invention is also an immunogenic composition, characterized in that it comprises an active principle selected from the group consisting of:
a polynucleotide capable of expressing all or part of the NS1 protein of the dengue virus, whatever its serotype,
an expression system comprising at least one promoter capable of expressing, in the host into which it is injected, a DNA encoding the NS1 protein of the dengue virus, whatever its serotype, said DNA expressing said protein,
in combination with at least one pharmaceutically acceptable vehicle.

Vaccination protocols using nucleic acids are described in particular in international application WO 90/11092.

A subject of the present invention is the use of an NS1 protein of a flavivirus, in the hexameric form, or of a system for the expression thereof, for preparing an immunogenic composition capable of inducing the production of antibodies in vivo.

In a preferred method of said use, the NS1 protein is that of the dengue virus, in particular dengue virus serotype 1.

A subject of the present invention is also the use of at least one monoclonal anti-NS1 antibody having a high affinity for the NS1 protein in the hexameric form, said monoclonal antibodies then being purified, and modified, for manufacturing a medicinal product capable of inducing passive immunization.

Advantageously, the modifications to the antibodies are, in particular, the selection of Fab fragments or the humanization of the antibodies.

A subject of the present invention is also the use of the NS1 protein in the hexameric form, for selecting in vitro antibodies specific for said NS1 protein, able to diagnose an infection with a flavivirus, at an early stage.

In an advantageous embodiment of said use, the antibodies are polyclonal antibodies.

In another advantageous embodiment of said use, the antibodies are monoclonal antibodies.

In another advantageous embodiment of said use, the protein is the NS1 protein of the dengue virus, in particular dengue virus serotype 1.

The anti-NS1 monoclonal antibodies are advantageously obtained by fusing spleen cells from a mouse immunized with the NS1 protein in the hexameric form, with suitable myeloma cells.

A subject of the present invention is also a method for expressing a polynucleotide encoding the NS1 protein of a dengue virus, characterized in that it comprises the expression of a polynucleotide as defined in the sequence SEQ ID No. 1, associated with a promoter for said polynucleotide, in suitable eukaryotic cells.

Figure 1B:
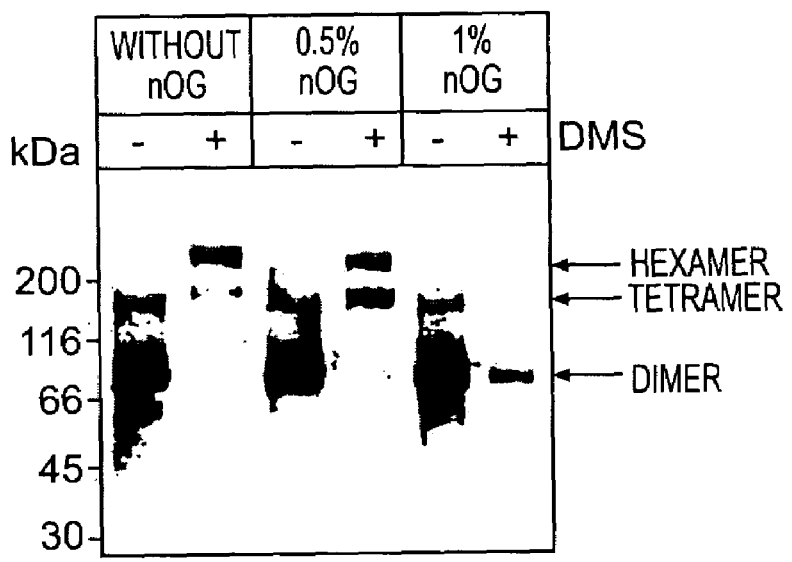

Other characteristics and advantages of the invention appear in the remainder of the description and the examples illustrated by the figures in which:

FIG. 1 represents the purified hexameric extracellular NS1 protein obtained after exclusion chromatography. (a) After exclusion chromatography, the protein is concentrated to 0.5 mg/ml by ultrafiltration and treated with dimethyl suberimidate (DMS) at 0, 0.5, 5 and 50 mM. The products obtained are placed in a nonreducing Laemmli buffer, separated on a 4 to 20% gradient acrylamide gel and stained with Coomassie blue. A sample-treated with 50 mM DMS is heated for 3 min at 95° C. before electrophoresis in order to dissociate the noncovalent oligomers. (b) The purified NS1 protein is treated overnight at 37° C. with 0.5% or 1% of n-octylglucoside (nOG) and, optionally, treated with 25 mM of DMS for 1 hour. The proteins are separated without heat denaturation on a 4 to 20% gradient acrylamide gel and detected via immunoblotting with a monoclonal anti-NS1 antibody from the literature or as defined above.

FIG. 2 represents the sequence of the NS1 protein of dengue virus serotype 1, obtained with clone 4 C of example 2 below, and also the corresponding coding sequence.

FIG. 3 illustrates the results obtained by assaying the circulating NS1 protein using the method of detection by capture-ELISA in patients infected beforehand with a dengue virus, whose sera were taken during the acute and convalescent phases, and also the comparison with the results obtained using the techniques of the prior art, IHA (inhibition of hemagglutination of dengue virus serotypes 1, 2, 3 or 4) and MAC ELISA (immunoglobulin *M Antibody Capture Enzyme-Linked ImmunoSorbent Assay*); D1 corresponds to dengue serotype 1; D2 corresponds to dengue serotype 2; D3 corresponds to dengue serotype 3 and D4 corresponds to dengue serotype 4; ID=patient's identity; 1 corresponds to the first sample in the acute phase of the disease, 2 corresponds to the second sample in the convalescent phase (taken 2 to 4 weeks after the first); in the capture-ELISA assay, the values are expressed as optical density obtained for the same serum diluted 10, 30 or 90 times.

FIG. 4 illustrates the detection of the NS1 protein using the capture-ELISA assay on sera from patients infected with dengue virus serotype 1 from French Guiana. The numbers indicated represent the number of patients divided up per category (positivity or negativity by capture-ELISA and positivity or negativity for IgM).

Figure 5:
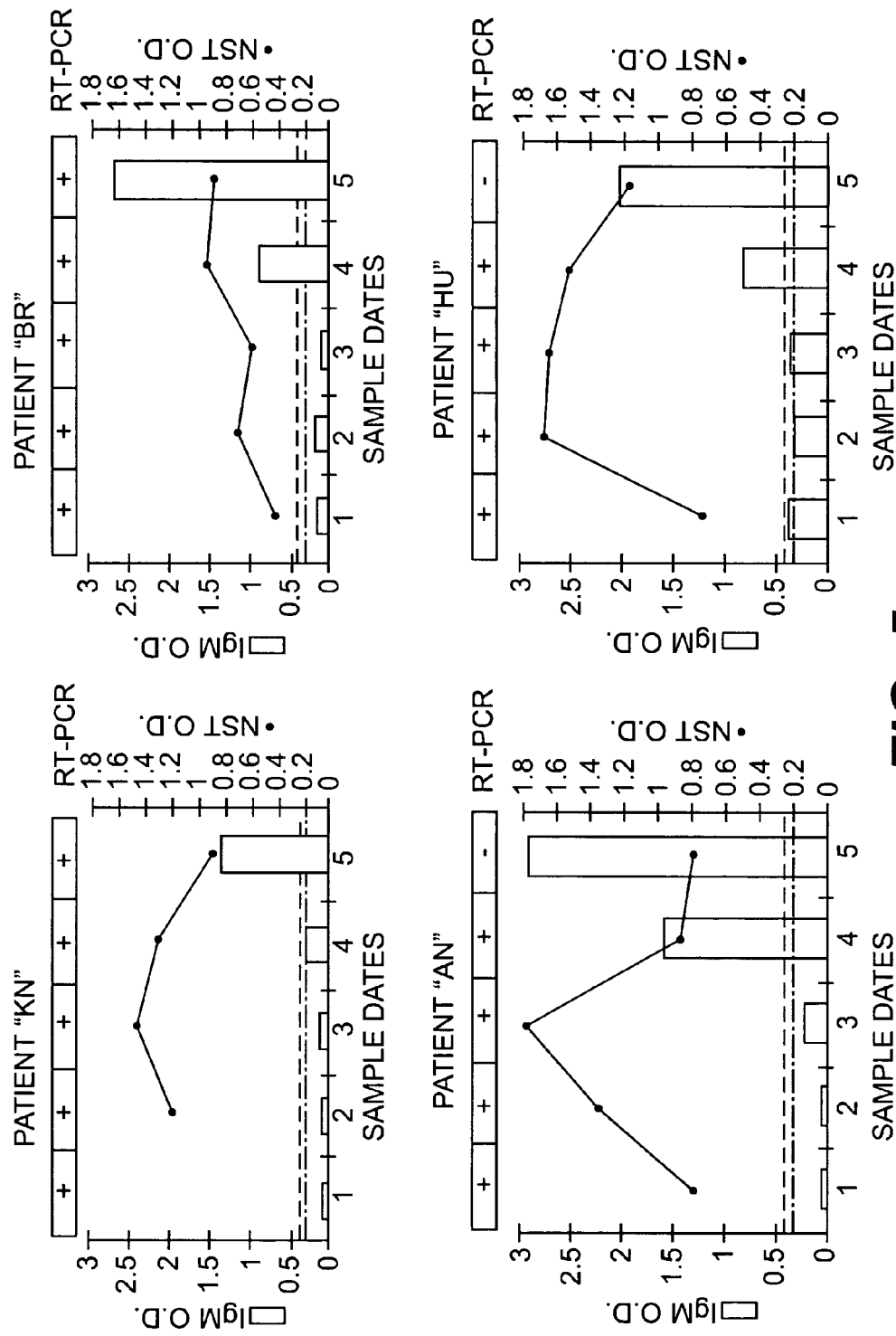

FIG. 5 illustrates the results obtained for 4 patients from French Guiana infected with dengue virus 1, from whom samples were taken daily during the clinical phase of the disease from D1 to D5. Each graph corresponds to a patient with, for each day on which a sample was taken, both the results of detection of the NS1 protein with the capture-ELISA assay developed, the results of RT-PCR and the results obtained using the MAC-ELISA technique. The O.D.

values reported were corrected for once the value of the background noise. The positivity thresholds are indicated by the broken lines.

FIG. 6 indicates the characteristics of the anti-NS1 monoclonal antibodies F22 and G18.

FIG. 7 illustrates the detection of the NS1 protein with the capture-ELISA, assay using the monoclonal approach in comparison with the capture-ELISA assay using the polyclonal approach as described in example 3. The results obtained are reported in the form of optical density values measured for each dilution of serum analyzed (10th, 30th or 90th) and less the mean value of the negative controls.

FIG. 8 illustrates the demonstration of the NS1 protein in the sera from patients infected with the yellow fever virus, using an capture-ELISA assay specific for yellow fever. For each serum tested, the optical density value measured using the assay developed, less the mean value of the negative controls, the optical density value measured using the MAC-ELISA assay specific for yellow fever IgMs and the results of the viral isolation, when they are available, are reported.

EXAMPLE 1

Purification of the NS1 Protein of Dengue Virus Serotype 1

1. Materials and Methods

The protein is produced on Vero cells infected with dengue virus serotype 1, strain FGA/89 (P. Després et al., Virol, (1993), 196, 209-219), under the conditions adapted for the method described by A. K. I. Falconar et al., (*J. Virol. Meth*, (1990), 30, 323-332).

The culture medium is harvested 5 days after infection and centrifuged at 1500 g to remove the cellular debris. The centrifugation supernatant is brought to 20 mM Tris-HCl, mM sodium azide, and concentrated 6 times by cold ultrafiltration, and the viral particles are removed by precipitation for 2 h at 4° C., with a concentration of 7.5% of polyethylene glycol (PEG), followed by centrifugation for 30 minutes at 10 000 g. The clarified, supernatant, containing 7.5% PEG is treated with 0.05% Tween 20 and 1 mg/ml of aprotinin, and then passed over an immunoaffinity column to which is attached an anti-NS1 monoclonal antibody. The protein is eluted according to the diethylamine technique, as described in Falconar et al., (mentioned above), and concentrated by ultrafiltration, and the elution solution is exchanged with a 10 mM Tris-HCl buffer, pH 7.5, containing 1 mM of sodium azide.

2. Results

The results are illustrated in FIG. 1.

FIG. 1*a* shows that the NS1 protein is indeed in the hexameric form. The proportion of hexameric form increases with an increase in concentration of DMS (FIG. 1*a*).

The extracellular NS1 protein in the hexameric form may be transformed into dimeric subunits in the presence of the nonionic detergent n-octylglucoside (nOG) (FIG. 1*b*). After incubation overnight at 37° C. in the presence or absence of n-octylglucoside (nOG) and treatment with 25 mM DMS, it is observed that, in the absence of nOG, bands are present which correspond to the dimer, to the tetramrer and to the hexamer, and that, in the presence of nOG, there is partial or complete dissociation of the hexamer depending on the concentration of nOG (FIG. 1*b*).

EXAMPLE 2

Expression of the NS1 Protein of Dengue Virus Serotype 1 by Vero Cells

1. Materials and Methods

The pCIneo-NS1.FGA plasmid (deposited with the Collection Nationale de Cultures et de Microorganismes [National collection of cultures and microorganisms] (CNCM) of the Institut Pasteur under the No. I-2220, dated Jun. 7, 1999) containing the gene of the NS1 protein comprising the gene encoding its signal peptide, preceded by a translation initiation codon and followed by a translation termination codon, is introduced into the competent bacterium *Escherichia coli* (epicurian SURE from Stratagène). This plasmid is amplified in bacterial culture and purified according to the conventional technique for preparing plasmid DNA. The purified DNA is used to sequence various clones (the sequence of clone 4 C is illustrated in FIG. 2) and to transfect Vero cells using either a suitable mixture with cationic liposomes, such as DOTAP (Boehringer Mannheim), or with a nonliposomal agent, such as FuGENE (Boehringer Mannheim). The FuGENE and the DNA are pre-incubated in medium without serum for 15 min, and then the mixture is brought into contact with a layer of Vero cells for 24 h. The cells are then rinsed with PBS (phosphate buffered saline), fixed for 20 min at room temperature with a solution of. PBS containing 3% of paraformaldehyde and permeabilized for 5 min with PBS containing 0.5% Triton X-100. The presence of NS1 antigen is then revealed using specific antibodies, which are recognized by a fluorosceinlabeled conjugated antibody.

2. Results

It is thus possible to demonstrate a strong fluorescent signal, specific for the NS1 viral antigen, in approximately 20% of the transfected cells.

The expression of NS1 is thus demonstrated and stable lines may be established in the presence of neomycin, which is a selection marker for the transfected cells.

FIG. 2 illustrates the sequence of the NS1 protein of dengue virus serotype 1 thus obtained, and also the corresponding coding sequence.

EXAMPLE 3

Implementation of the Capture-ELISA Technique According to the Invention in the Context of an Infection with Dengue Virus Serotype 1 and Comparison with the Methods of the Prior State of the Art 1. Principle of the Capture-ELISA Technique The NS1 viral antigen is captured using monospecific mouse polyclonal antibodies purified beforehand by immunocapture on the purified hexameric NS1 protein of dengue serotype 1.

The presence of NS1 is revealed using antibodies from rabbits immunized with the purified hexameric NS1 protein, themselves recognized by antibodies conjugated to horseradish peroxidase.

2. Materials and Methods a—Purification of Mouse Polyclonal Antibodies Directed Against the NS1 Protein a₁—Attachment of the NS1 Protein to a Membrane The purified NS1 protein is attached by adsorption to an amphoteric nylon membrane (Nytran, Schleicher & Schuell). The surface of the membrane is then saturated with bovine albumin present at a concentrate of 3% in a phosphate buffered saline solution (PBS; 10 mM phosphate; pH 7.2; 150 mM NaCl). After 2 rinses in PBS, the membrane is treated with PBS containing 0.25% of glutaraldehyde for 15 min at room temperature. After 3 rinses in PBS, the membrane is neutralized with a 100 mM glycine buffer containing 3% bovine albumin, rinsed twice in PBS and then stored at 4° C. in PBS with 1 mM sodium azide.

a₂—Purification of the Mouse Monospecific Polyclonal Antibodies (Capture Antibodies)

production of polyclonal ascites: the brains of young Swiss mice infected with dengue virus and moribund are ground in 9 ml of PBS buffer. The product is centrifuged for 10 min at 10 000 g at 4° C.

The viral suspension is injected into Swiss mice, according to the following calendar of events:

D0: 0.5 ml of antigen subcutaneously into the thigh,
D3: 0.4 ml of antigen and 0.1 ml of complete Freund's adjuvant intraperitoneally,
D25: 0.5 ml of antigen intraperitoneally,
D26: 0.5 ml of TG180 mouse ascites, and
D28: 0.5 ml of antigen intraperitoneally.

The ascites are harvested on D42.

After having collected the ascites, the coagulum is allowed to form for 1 hour at room temperature and then centrifugation is carried out for at least 30 min at 1500 g. The supernatant is left to stand overnight at 4° C. The pH of the supernatant is adjusted to 4.8 with 2M acetic acid and the supernatant is then centrifuged again under the same conditions. The pH of the supernatant is then brought to 7.0-7.2 by adding a 2N sodium hydroxide solution. The supernatant may be stored at −20° C.

Purification of the Mouse Antibodies Specific for Dengue Virus Serotype 1:

The membrane is incubated for one hour at room temperature in a mixture of polyclonal ascites directed against the 4 dengue virus serotypes prepared as described above.

After rinsing the membrane 3 times in PBS, the antibodies attached to the NS1 protein are eluted with a diethylamine solution, pH 11.4 (Dubelco medium modified with Iscove (Gibco) containing 100 mM diethylamine). The antibodies are concentrated by ultrafiltration and returned to a PBS buffer containing 1 mM sodium azide.

b—Preparation of Rabbit Polyclonal Antibodies Directed Against the NS1 Protein (Revelation Anti-Bodies):

The rabbits were immunized with 3 or 4 successive injections of 30 μg of hexameric NS1 protein purified according to the method of example 1, given on D0, D7, D21 and, optionally, on D49, and followed by bleeding out on D83. The serum is depleted of nonspecific signal by incubation with Sepharose beads bearing a monoclonal antibody described in the literature or prepared as described above.

c—Capture-ELISA Method c₁—Standard Curve

For each capture-ELISA plate intended for testing human sera, a standard range is prepared from a solution of NS1 protein purified according to the method described in point 1, the initial concentration of which is 0.5 pg/ml, and which is diluted in 3-fold serial dilutions.

C₂—Detection of the Circulating NS1 Protein During the Acute Phase:

The purified mouse polyclonal antibodies obtained according to the method described above (capture antibodies) are attached to a plate, diluted in a PBS solution and left to incubate overnight at 4° C. After 3 rinses for 5 minutes with a solution of PBS/0.05% Tween, the plate is saturated with a mixture of PBS, 0.05% Tween and 3% milk for 30 minutes at room temperature. After 3 rinses with a solution of PBS/0.05% Tween, the sera to be tested, diluted or undiluted, are deposited and left to react for one hour, still at room temperature. The 1/10th, 1/30th and 1/90th dilutions are prepared in a solution of PBS/0.05% Tween. After 3 rinses, the second antibody specific for NS1 (revelation antibody obtained in point 3 above) is added, after having been diluted in a mixture of PBS/0.05% Tween and of 3% milk, and left to incubate for 45 minutes at 37° C. After 3 rinses, the anti-IgG antibodies are directed against the second antibody and labeled with peroxidase, said antibody being prepared under conventional conditions known to those skilled in the art, is added and the incubation is carried out for 45 minutes at 37° C. After 3 rinses, revelation is carried out for 10 minutes with a solution of TMB (3,3',5, 5'-tetramethylbenzidine, Kierkegaard & Perry Lab). The colorimetric reaction is stopped with sulfuric acid.

3. Results

They are illustrated in FIG. 3.

The capture-ELISA technique according to the invention makes it possible to detect the presence of NS1 protein in the acute phase of the disease, this detection being independent of whether the patients have a primary or secondary infection.

The results confirm that the presence of the NS1 protein is transient, since this protein is not detected in the samples taken in the convalescent phase (FIG. 3).

93% of the samples taken in the acute phase of the disease prove to be negative using the MAC ELISA assay, whereas 100% of the samples taken in the convalescent phase prove to be positive in this same assay (FIG. 3).

Similarly, the inhibition of hemagglutination assay (IHA) does not make it possible to detect infection with dengue virus serotype 1 in 80% of cases in the acute phase of the disease, but this test proves to be positive in 100% of the samples taken in the convalescent phase (FIG. 3). According to the WHO criteria, an IHA level of less than 1280 in the serum taken in the convalescent phase allows diagnosis of a primary dengue infection and a level of greater than 1280 allows diagnosis of a secondary dengue infection.

Half of the positive sera in this study therefore correspond to cases of primary dengue and the other half to cases of secondary dengue. The capture-ELISA technique according to the invention thus makes it possible to detect the NS1 protein in cases of primary and secondary dengue.

EXAMPLE 4

Determination of the Detection Window

1. Materials and Methods a—Study Carried Out on a Population of Patients from French Guiana Infected with Dengue Virus 1

The samples are taken from patients infected with dengue virus serotype 1, between D0, marking the appearance of the clinical signs (initially a nondifferentiated fever) and D66 corresponding to the end of the convalescent phase.

The presence of circulating NS1 is sought in the sera of these patients, according to the capture-ELISA method described in example 3, and the result obtained is compared with the positivity for specific IgMs measured by MAC-ELISA, when the data are available.

b—Daily Monitoring of 4 Patients Infected with Dengue Virus 1

Samples were taken daily from 4 patients during the clinical phase from D1 to D5. An RT-PCR reaction to reveal the viral RNA, a MAC-ELISA assay to detect IgMs specific for dengue virus and a search for the dengue NS1 antigen according to the capture-ELISA method described above were carried out on each blood sample.

2. Results a—Determination of the Detection Window

The results are given in FIG. 4.

Between D1 and D6, the possibility of detecting the circulating NS1 protein oscillates between 64% (on D2) and 100% (on D5) of the infected patients. Beyond D10, the circulating NS1 protein is no longer detected, whereas the antibody response becomes predominant.

Detection of the circulating NS1 protein does not appear to be dependent on the presence of total IgMs (specific for the viral antigens) which appear, in certain cases, on D3 and culminate from D5, nor even, for certain patients, on the presence of total IgGs which may appear from D2. On the other hand, the absence of detection of the NS1 antigen in clinical phase sera may be explained by the presence of IgGs specifically directed against NS1.

Thus, the detection window for the NS1 antigen in the serum, using the capture-ELISA technique according to the present invention, is preferably between D1 and D6 after appearance of the clinical signs.

b—Daily Monitoring of 4 Patients Infected with dengue Virus

The results are given in FIG. 5.

In the 4 patients studied, the NS1 protein is detected continuously up to D5, this being regardless of the day on which the sample was taken relative to the start of symptoms. For certain patients, the detection window for the protein is wider than the period of viremia, detected by RT-PCR.

EXAMPLE 5

Implementation of the Capture-ELISA Technique with Monoclonal Tools in the Context of an Infection with Dengue Virus Serotype 1 and Comparison with the Capture-ELISA Technique Described Above 1. Materials and Methods a—Production and Characterization of Mouse Monoclonal Antibodies Directed Against the NS1 Protein of Dengue Virus Serotype 1

$a_1$—Production of Mouse Monoclonal Antibodies Directed Against the NS1 Protein Female Balb/C mice were immunized with 7 injections of 10 µg of hexameric NS1 protein of dengue virus serotype 1, purified according to the method of example 1. The first injection in complete Freund's adjuvant and the subsequent five injections in incomplete Freund's adjuvant are given subcutaneously 15 days apart. The final injection, in incomplete Freund's adjuvant, given three days before the animal is sacrificed, is given intraperitoneally.

The cells from the spleen of the immunized mice are fused with the murin myeloma and cultured until clones appear, according to standard protocol.

$a_2$—Identification of Hybridomas Secreting Anti-NS1 Antibodies

Antibodies specific for the NS1 protein were detected either using a conventional ELISA technique or using a capture-ELISA technique.

Conventional ELISA Technique

The hexameric NS1 protein purified according to the method of example 1 is attached to a plate by adsorption, at the concentration of 1 µg/ml in a PBS solution overnight at 4° C. After 3 washes with a solution of PBS/0.1% Tween (PT), the protein is incubated with the supernatants of the various hybridomas diluted two-fold with a solution of PT containing 0.5% gelatin (PTG), for 1 h at 37° C. After 3 washes with PT, the peroxidase-labeled anti-mouse IgG antibody diluted in PTG is added and incubated for 1 h at 37° C. After 3 washes, revelation is carried out with a solution of hydrogen peroxide in the presence of orthophenylenediamine.

Capture-ELISA Technique

The technique used is described in example 3 (cf. detection of the circulating -NS1protein in the acute phase), but replacing the dilutions of sera to be tested with a 1/10th dilution, in the PTG solution, of culture supernatant on uninfected Vero cells or Vero cells infected for 5 days-with dengue-virus serotype1, and precipitated with 7% of polyethylene glycol (cf. example 1: purification of the NS1 protein of dengue virus serotype 1). The reactivity of the supernatants from the various hybridomas with respect to the culture supernatant from uninfected Vero cells is used as a control for nonspecific signal.

$a_3$—Reactivity of the Anti-NS1 Monoclonal Antibodies, by Indirect Immunofluorescence, on Vero Cells Infected with One of the 4 Dengue Virus Serotypes The Vero cells are infected for 40 h with one of the 4 dengue virus serotypes:

serotype 1: strain FGA/89
serotype 2: strain NG
serotype 3: strain H87
serotype 4: strain H241

After 1 wash with a solution of PBS, the cells are fixed with a solution of 3% paraformaldehyde in PBS for 30 minutes at laboratory temperature. The cells rinsed in PBS are then permeabilized with a solution of 0.5% Triton X-100 in PBS for 10 minutes. After rinsing in PBS, the cells are incubated for 1 h with the supernatants from the various hybridomas which have reacted positively by ELISA. After 3 washes with PBS, the fluorescene-labeled anti-mouse IgG antibody is added and incubated for 1 h. After 3 washes in PBS, the slides are covered with a coverslip and observed under a fluorescent microscope.

a4—Preparation of the Mouse Monoclonal Ascites

The monoclonal ascites are produced in Balb/C mice. The mice are given an intraperitoneal injection of 0.5 ml of pristane (2,6,10,14-tetramethylpentadecane, Sigma) one week before the intraperitoneal injection of the hybridoma clone secreting the monoclonal antibody. The ascites are removed as they form, centrifuged at 1500 rpm for 20 minutes and stored at −20° C.

a₅—Determination of the Isotype of the Anti-NS1 Monoclonal Antibodies

The isotype of the anti-NS1 antibody is determined by ELISA using antibodies directed against the various murine immunoglobulin subclasses: IgG1, IgG2a, IgG2b and IgG3. The light chain of the immunoglobulin is determined according to an identical methodology.

a6—Determination of the Affinity Constant of the anti-NS1 Monoclonal Antibodies (B Friguet et al., *J. Immunol,* (1985), 77, 305-319)

The affinity of an antibody corresponds to the concentration of antigen required to saturate 50% of the sites of the antibodies. An incubation is carried out in liquid medium between the antibody at constant concentration and the antigen at decreasing concentration overnight at 4° C. in order to reach the equilibrium of the reaction. The concentration of free antibodies, after equilibrium, is determined using an ELISA assay: the mixture is deposited onto a plate preincubated with the antigen. After incubation for 20 minutes at 4° C. (to avoid a shift of the equilibrium), the ELISA is revealed with a β-galactosidase-coupled anti-mouse IgG, followed by the enzymatic reaction. The dissociation constant KD is then determined.

a₇—Competition Reaction for the various Anti-NS1 Monoclonal Antibodies

This reaction makes it possible to determine the specificity of the monoclonal antibodies with respect to the same epitope or to different epitopes. Epitope determination brings into play the reactivity for an antigen, of an unlabeled monoclonal antibody and of a second-monoclonal antibody, coupled to biotin.

The first monoclonal antibody, unlabeled, is placed at saturating concentration (determined beforehand by ELISA) on a plate to which the antigen has been attached beforehand, and incubated for 2 h at 37° C. After 4 washes in PT solution at 4° C., the second monoclonal antibody, coupled to biotin, is added and incubated for 20 minutes at 4° C. After 4 washes in PT solution at 4° C., the solution of peroxidase-labeled streptavidin conjugate is added and incubated for 1 h at 37° C. After 4 washes in PT solution, the complex is revealed with a solution of hydrogen peroxide in the presence of orthophenylenediamine. If a signal is obtained after reading on a spectrophotometer, this indicates that the epitopes recognized by the 2 antibodies are different. If the opposite is true, the 2 monoclonal antibodies are directed against the same epitope of the antigen.

b—Purification of the Monoclonal Antibodies G18 and F22

The antibodies G18 and F22 are purified by immunoaffinity as described in Exmaple 3.

c—Detection of the Circulating NS1 Protein with a Capture-ELISA Assay Using the Monoclonal Antibodies The purified monoclonal antibodies G18 and F22 are mixed in a solution of PBS at a given dilution and incubated overnight at 4° C. The subsequent steps of this ELISA assay are similar to those of the previous example.

d—Comparison of the capture-ELISA Assay Using the Monoclonal Approach with that Using the Polyclonal Approach A panel of serum from French Guiana was tested on the same day with the capture-ELISA assay using the monoclonal approach and then using the polyclonal approach. The sera are tested at various dilutions: 10th, 30th and 90th.

2. Results a—Characteristics of the Monoclonal Antibodies

The results are given in FIG. 6.

The antibodies G18 and F22 were selected for their ability to bind, with high affinity, to different epitopes of the NS1 protein. The antibody F22 is specific for dengue virus serotype 1, and G18 is specific for dengue virus serotypes 1 and 3.

b 1'Use of the Monoclonal Antibodies for NS1 Antigen Capture

The results are given in FIG. 7.

The monoclonal antibodies selected not only reproduce the results obtained with the polyclonal approach, but they exhibit more marked reactivities than the polyclonal antibodies. The monoclonal tool developed therefore appears to be particularly suitable for the diagnostic use which must be made of it.

EXAMPLE 6

Implementation of the Capture-ELISA Technique According to the Invention in the Context of an Infection with Another Dengue Virus Serotype or Another Flavivirus 1. Materials and Methods a—Preparation of Culture Supernatants The Vero cells are infected either with dengue virus 2 or with the Japanese encephalitis virus or the yellow fever virus. The culture supernatants are then prepared according to the method described in example 1.

b—Purification of the Monoclonal Antibodies Directed Against the NS1 Protein of the Yellow Fever Virus and of the Japanese Encephalitis Virus The monoclonal ascites of the antibodies 8G4, 1A5 and 2D10 (J. J. Schlesinger et al., *Virology,* (1983), 125, 8-17) directed against the NS1 protein of the yellow fever virus, and of the antibodies 171-2-2 and 70-14-20 directed against the NS1 protein of the Japanese encephalitis virus, are purified on protein A Sepharose CL-4B beads (Pharmacia Biotech). These monoclonal ascites are incubated overnight at 4° C. on the protein A beads. After the beads have been rinsed 3 times in PBS/0.05% Tween, the antibodies attached to the protein A beads are eluted with a solution of glycine buffer, pH=3. They are then concentrated by ultrafiltration and returned to a PBS buffer containing 1 mM sodium azide.

c—Detection of the NS1 Protein in the Dengue Virus 2 Culture Supernatants c₁—Antibodies Used The capture step is carried out with a mixture of ascites of the monoclonal antibodies 3D1.4 and 1A12 (A. K. I. Falconar et al., *Arch. Virology,* (1994), 137, 315-326). The protein is then recognized with a mixture of two rabbit antibodies: the serum obtained after immunization with the purified protein described in example 3 and a rabbit serum obtained after immunization with the viruses of the four dengue serotypes.

c₂—Capture-ELISA Method

The technique used is the same as that described in example 3.

d—Detection of the NS1 Protein in the Japanese Encephalitis Virus Culture Supernatants d₁—Antibodies Used The purified monoclonal antibodies 171-2-2 and 70-14-20 are used for the capture step. The protein is then recognized with a mixture of two sera from rabbits which have been immunized beforehand with recombined proteins of the NS1 protein of Japanese encephalitis.

d₂—Capture-ELISA Method

The technique used is the same as that described in example 3.

e—Detection of the NS1 Protein in the Yellow Fever Virus Culture Supernatants and the sera from Patients Infected with this Virus e₁—Antibodies Used The purified monoclonal antibodies 8G4, 1A5 and 2D10 are mixed, at a given dilution, in a solution of PBS and used as capture antibodies. The second antibody specific for yellow fever NS1 used originates from a serum of a rabbit immunized beforehand against the NS1 protein of the yellow fever 17D virus (J. J. Schlesinger et al., *J. immunol.* (1985), 135, 2805-2809).

e₂—Capture-ELISA Method

The technique used is the same as that described in example 3.

2. Results

Secretion of the NS1 protein has previously been reported in in vitro cell cultures infected with various flaviviruses, the DEN2 virus (Winkler et al., *Virology* (1988), 162, 187-196, Pryor et al., *Virology* (1993) 194, 769-780), the tick-borne encephalitis virus (Lee et al., *J. Gen. Virol.* (1989), 70, 335-343, Crooks et al., *J. Chrom.* (1990), 502, 59-68, Crooks et al., *J. Gen. Virol.* (1994), 75, 3453-3460), the Japanese encephalitis virus (Mason, *Virology* (1989), 169, 354-364, Fan et al., *Virology.* (1990), 177, 470-476), the Murray valley encephalitis virus (Hall et al., *J. Virol. Meth.* (1991), 32, 11-20) and the yellow fever virus (Post et al., *Vir. Res.* (1990), 18, 291-302). As these results were obtained using different ELISA techniques, we sought to demonstrate the protein, using the capture-ELISA technique of the present invention, in supernatants of infected mammalian cells.

The NS1 protein is detectable in the culture supernatants of the Vero cells infected either with the DEN2 virus, with the Japanese encephalitis virus or with the yellow fever virus.

It was also possible to demonstrate the protein, using this technique, in sera from patients infected with the yellow fever virus, as demonstrated by the results given in FIG. 8. Among the 18 sera generously provided by Ch. Mathiot (Institut Pasteur of Dakar), 7 are positive by NS1 antigenemia, and, as for the DEN1 virus, detection of the circulating NS1 protein appears to be indifferent to the presence of IgMs specific for yellow fever.

The capture-ELISA technique according to the present invention makes it possible to detect the NS1 protein in the culture supernatants of cells infected with various flaviviruses and in the sera from patients infected with the yellow fever virus. Because of this, it may have a diagnostic application for detecting an infection with a flavivirus other than the DEN1 virus.

SEQUENCE LISTING

```
<160> NUMBER OF SEQ ID NOS: 2

<210> SEQ ID NO 1
<211> LENGTH: 1137
<212> TYPE: DNA
<213> ORGANISM: Dengue virus type 1
<220> FEATURE:
<221> NAME/KEY: CDS
<222> LOCATION: (1)..(1134)

<400> SEQUENCE: 1 atg agg agc gcg tcg ctt tcg atg acg tgc att gca gtt ggc atg gtt      48
Met Arg Ser Ala Ser Leu Ser Met Thr Cys Ile Ala Val Gly Met Val
  1               5                  10                  15 aca ctg tac cta gga gtc atg gtt caa gcg gac tcg gga tgt gta atc      96
Thr Leu Tyr Leu Gly Val Met Val Gln Ala Asp Ser Gly Cys Val Ile
             20                  25                  30 aac tgg aag ggc aga gaa ctc aaa tgt gga agt ggc att ttt gtc act     144
Asn Trp Lys Gly Arg Glu Leu Lys Cys Gly Ser Gly Ile Phe Val Thr
         35                  40                  45 aat gaa gtc cac act tgg aca gag caa tac aaa ttc cag gct gac tcc     192
Asn Glu Val His Thr Trp Thr Glu Gln Tyr Lys Phe Gln Ala Asp Ser
     50                  55                  60 cca aaa aga ctc tca gca gcc att ggg aag gca tgg gag gag ggc gtg     240
Pro Lys Arg Leu Ser Ala Ala Ile Gly Lys Ala Trp Glu Glu Gly Val
 65                  70                  75                  80
```

| | | |
|---|---|---|
| tgt gga att cga tca gcc acg cgt ctt gag aac atc atg tgg aag caa<br>Cys Gly Ile Arg Ser Ala Thr Arg Leu Glu Asn Ile Met Trp Lys Gln<br>85 90 95 | | 288 |
| ata tca aat gaa ttg aac cac att cta ctt gaa aat gac atg aaa ttc<br>Ile Ser Asn Glu Leu Asn His Ile Leu Leu Glu Asn Asp Met Lys Phe<br>100 105 110 | | 336 |
| aca gtg gtt gta gga gat gct aat gga att ttg gcc cag ggg aaa aaa<br>Thr Val Val Val Gly Asp Ala Asn Gly Ile Leu Ala Gln Gly Lys Lys<br>115 120 125 | | 384 |
| atg atc agg cca caa ccc atg gaa cac aaa tac tca tgg aaa agc tgg<br>Met Ile Arg Pro Gln Pro Met Glu His Lys Tyr Ser Trp Lys Ser Trp<br>130 135 140 | | 432 |
| gga aaa gcc aag atc ata gga gca gac aca cag aat acc acc ttc atc<br>Gly Lys Ala Lys Ile Ile Gly Ala Asp Thr Gln Asn Thr Thr Phe Ile<br>145 150 155 160 | | 480 |
| atc gac ggc cca gac act cca gaa tgc ccc gat gac caa aga gcg tgg<br>Ile Asp Gly Pro Asp Thr Pro Glu Cys Pro Asp Asp Gln Arg Ala Trp<br>165 170 175 | | 528 |
| aac att tgg gaa gtt gag gac tat ggg ttt gga att ttc acg aca aac<br>Asn Ile Trp Glu Val Glu Asp Tyr Gly Phe Gly Ile Phe Thr Thr Asn<br>180 185 190 | | 576 |
| ata tgg ctg aaa ttg cgt gac tcc tac acc caa atg tgt gac cac cgg<br>Ile Trp Leu Lys Leu Arg Asp Ser Tyr Thr Gln Met Cys Asp His Arg<br>195 200 205 | | 624 |
| cta atg tca gct gcc gtc aag gac agc aag gca gtc cat gct gac atg<br>Leu Met Ser Ala Ala Val Lys Asp Ser Lys Ala Val His Ala Asp Met<br>210 215 220 | | 672 |
| ggg tac tgg ata gaa agt gaa aag aac gag acc tgg aag cta gcg aga<br>Gly Tyr Trp Ile Glu Ser Glu Lys Asn Glu Thr Trp Lys Leu Ala Arg<br>225 230 235 240 | | 720 |
| gcc tcc ttc ata gaa gtc aag aca tgc att tgg ccg aaa tcc cac act<br>Ala Ser Phe Ile Glu Val Lys Thr Cys Ile Trp Pro Lys Ser His Thr<br>245 250 255 | | 768 |
| cta tgg agt aat gga gtt ttg gaa agt gaa atg ata atc cca aag ata<br>Leu Trp Ser Asn Gly Val Leu Glu Ser Glu Met Ile Ile Pro Lys Ile<br>260 265 270 | | 816 |
| tat gga gga cca ata tct cag cac aat tac aga cca ggg tat ttc aca<br>Tyr Gly Gly Pro Ile Ser Gln His Asn Tyr Arg Pro Gly Tyr Phe Thr<br>275 280 285 | | 864 |
| caa aca gca ggg cca tgg cac cta ggt aag ttg gaa ttg gat ttt gac<br>Gln Thr Ala Gly Pro Trp His Leu Gly Lys Leu Glu Leu Asp Phe Asp<br>290 295 300 | | 912 |
| ttg tgt gaa ggc acc aca gtt gtt gtg gat gaa cat tgt gga aat cga<br>Leu Cys Glu Gly Thr Thr Val Val Val Asp Glu His Cys Gly Asn Arg<br>305 310 315 320 | | 960 |
| ggt cca tct ctc aga act aca aca gtc aca gga aag ata atc cat gaa<br>Gly Pro Ser Leu Arg Thr Thr Thr Val Thr Gly Lys Ile Ile His Glu<br>325 330 335 | | 1008 |
| tgg tgt tgc aga tcc tgc acg tta ccc ccc tta cgc ttc aga gga gaa<br>Trp Cys Cys Arg Ser Cys Thr Leu Pro Pro Leu Arg Phe Arg Gly Glu<br>340 345 350 | | 1056 |
| gac gga tgt tgg tat ggc atg gaa atc aga cca gtt aag gag aag gag<br>Asp Gly Cys Trp Tyr Gly Met Glu Ile Arg Pro Val Lys Glu Lys Glu<br>355 360 365 | | 1104 |
| gag aac cta gtt agg tca atg gtc tct gca taa<br>Glu Asn Leu Val Arg Ser Met Val Ser Ala<br>370 375 | | 1137 |

<210> SEQ ID NO 2
<211> LENGTH: 378

```
<212> TYPE: PRT
<213> ORGANISM: Dengue virus type 1

<400> SEQUENCE: 2

Met Arg Ser Ala Ser Leu Ser Met Thr Cys

The invention claimed is:

1. A method for the early detection of a flaviviral infection comprising: detecting an NS1 nonstructural glycoprotein of a flavivirus in a biological sample by an immunological method using at least two antibodies, wherein the biological sample is obtained during the clinical phase of the infection, wherein the two antibodies may be identical or different, wherein a first antibody, called a capture antibody, which is unlabeled, is either (1) a polyclonal antibody with high affinity for NS1 protein of the flavivirus in hexameric form, wherein the polyclonal antibody is preselected by immunocapture with the NS1 protein in hexameric form, or (2) a mixture of purified anti-NS1 monoclonal antibodies preselected for their high affinity for the NS1 protein of the flavivirus, wherein the NS1 protein is in hexameric form, and, wherein a second antibody, called a revelation antibody, is a polyclonal antibody directed against the NS1 protein in hexameric form or a mixture of monoclonal antibodies directed against NS1 protein in hexameric form.

2. The method as claimed in claim 1, wherein the flaviviral infection is an infection of the dengue virus.

3. The method as claimed in claim 1, wherein the first antibody is attached to a solid support and the second antibody is optionally conjugated to a label.

4. The method as claimed in claim 3, wherein if the second antibody is not conjugated to a label, binding of the second antibody to the NS1 protein attached to the solid support is detected with a third antibody conjugated to a label.

5. The detection method as claimed in claim 4, wherein the label conjugated to the third antibody is an enzyme.

6. The detection method as claimed in claim 5, wherein
(A) the first antibody is a mouse polyclonal antibody selected by immunocapture of the NS1 protein of the dengue virus, wherein the NS1 protein is in hexameric form,
(B) the second antibody is a polyclonal antibody from a rabbit immunized with the NS1 protein of dengue virus serotype 1, wherein the NS1 protein is in hexameric form, and
(C) the third antibody reveals binding of the second antibody to NS1 protein, and the third antibody is an antibody conjugated to peroxidase and directed against the second antibody.

* * * * *

UNITED STATES PATENT AND TRADEMARK OFFICE
CERTIFICATE OF CORRECTION

PATENT NO. : 7,282,341 B2  Page 1 of 1
APPLICATION NO. : 11/017048
DATED : October 16, 2007
INVENTOR(S) : Marie Flamand et al.

It is certified that error appears in the above-identified patent and that said Letters Patent is hereby corrected as shown below:

Title Page of the Description Column 2

Item [57], line 5, "immumological" should read --immunological--.

Item [57], line 7, "pre-selected" should read --preselected--.

Signed and Sealed this

Twenty-fifth Day of December, 2007

JON W. DUDAS
*Director of the United States Patent and Trademark Office*